(12) United States Patent
Lemaire

(10) Patent No.: US 6,566,327 B1
(45) Date of Patent: May 20, 2003

(54) HISTOGRANIN PEPTIDES AND THEIR ANALGESIC USE

(75) Inventor: Simon Lemaire, Aylmer (CA)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 09/530,123

(22) PCT Filed: Oct. 26, 1998

(86) PCT No.: PCT/CA98/01002

§ 371 (c)(1),
(2), (4) Date: Jul. 6, 2000

(87) PCT Pub. No.: WO99/21877

PCT Pub. Date: May 6, 1999

(30) Foreign Application Priority Data

Oct. 24, 1997 (CA) .............................................. 2219437
Feb. 24, 1998 (CA) .............................................. 2224066

(51) Int. Cl.[7] .......................... A61K 38/04; C07K 5/10; C07K 5/12; C07K 7/08; C07K 7/64

(52) U.S. Cl. .......................... 514/11; 514/15; 514/16; 514/17; 514/18; 530/321; 530/328; 530/329; 530/330

(58) Field of Search ................................... 514/9, 11, 15, 514/16, 17, 18; 530/317, 321, 328, 329, 330

(56) References Cited

U.S. PATENT DOCUMENTS

| | | | |
|---|---|---|---|
| 4,416,871 A | 11/1983 | Walter et al. ............... 424/177 |
| 4,631,270 A | 12/1986 | Yankeelov, Jr. et al. ....... 514/15 |
| 5,169,833 A | 12/1992 | Hansen, Jr. et al. .......... 514/17 |
| 5,216,124 A | 6/1993 | Hansen, Jr. et al. ......... 530/317 |
| 5,364,842 A | 11/1994 | Justice et al. ................. 514/12 |
| 5,464,821 A | * 11/1995 | Stig et al. ..................... 514/18 |
| 5,470,753 A | * 11/1995 | Sepetov et al. ............... 436/89 |
| 5,656,267 A | 8/1997 | Sagen et al. .............. 424/93.21 |
| 5,807,828 A | 9/1998 | Scarborough ................. 514/16 |
| 5,811,391 A | 9/1998 | Arrhenius et al. ............ 514/11 |
| 5,817,750 A | 10/1998 | Ruoslahti et al. ........... 530/317 |

FOREIGN PATENT DOCUMENTS

| | | | |
|---|---|---|---|
| CA | 2097533 | 12/1993 | ............ C07K/7/08 |
| WO | WO9526362 | 10/1995 | ........... C07K/14/40 |
| WO | WO9606626 | 3/1996 | .......... A61K/38/00 |

OTHER PUBLICATIONS

Abstract, Society for Neuroscience, vol. 23, Oct. 25–30, 1997. Peptide Receptors: Structure and Function p674, Section 267.13.

Stacey Schultz–Cherry, "Regulation of Transforming Growth Factor–β Activation by Discrete Sequences of Thrombospondin 1". vol. 270. No. 13, Issue of Mar. 31, 1995, pp. 7304–7310. J. Biol Chem.

Richard S. Johnson, et al., "Novel Fragmentation Process of Peptides by Collision–Induced Decomposition in a Tandem Mass Spectrometer: Differentiation of Leucine and Isoleucine.", *Anal. Chem.* 1987, 59 pp. 2621–2625.

Thomas Hoeg–Jensen, Arno F. Spatola and Arne Holm, "Amino Monothio Acids in solid–phase Synthesis of Peptide Thioamides", *Int. J. Peptide Protein Res.* 47. 1996, pp. 190–200.

(List continued on next page.)

Primary Examiner—Jeffrey E. Russel
(74) Attorney, Agent, or Firm—Lahive & Cockfield, LLP; Jane E. Remillard, Esq.; Richa Nand, Esq.

(57) ABSTRACT

The invention relates to linear and cyclic peptide and pseudopeptide compounds useful as analgesics, pharmaceutical compositions comprising such compounds, the use of the compounds and the compositions in the treatment of pain, and commercial packages containing such compounds and compositions.

12 Claims, 4 Drawing Sheets

OTHER PUBLICATIONS

Julie B. Seigan and Jacqueline Sagen., "A natural Peptide with NMDA inhibitory Activity reduces tonic pain in the Formalin Model." vol. 8, No. 6. Apr. 14, 1997, pp. 1379–1381, Neuroreport.

Julie B. Siegan et al., "Suppression of Neuropathic Pain by a Naturally–derived Peptide with NMDA Antagonist Activity." *Brain Research* 755 (1997) pp. 331–334.

Hama AT, Siegan JB, Herzberg U, Sagen J., "NMDA–induced spinal hypersensitivity is reduced by naturally derived peptide analog [Ser 1]histogranin.", *Pharmacol Biochem Behav* 1999 Jan.;62(1):67–74.

Maurice T, Privat A, Lemaire S., Corrigendum to 'The pentadecapeptide [Ser1]histogranin impairs passive avoidance learning in mice', *Eur J Pharmacol*, Dec. 12, 1995;287(2):219. *Eur. J. Pharmacol.* 283 (1995) 251–4.

Maurice T, Privat A, Lemaire S., "The pentadecapeptide [Ser1]histogranin impairs passive avoidance learning in mice.", *Eur J Pharmacol*, Sep. 5, 1995;283(1–3):251–4.

Lemaire S, Rogers C, Dumont M, Shukla VK, Lapierre C, Prasad J, Lemaire, I., "Histogranin, a modified histone H4 fragment endowed with N–methyl–D–aspartate antagonist and immunostimulatory.", *Life Sci* Mar. 3, 1995;56(15):1233–41.

Prasad JA, Shukla VK, Lemaire S., "Synthesis and biological activity of histogranin and related peptides.", *Can J Physiol Pharmacol* Feb. 1995;73(2):209–14.

Shukla VK, Lemaire S, Dumont M, Merali Z., "N–methyl–D–aspartate receptor antagonist activity and phencyclidine–like behavioral effects of the pentadecapeptide, [Ser1]histogranin.", *Pharmacol Biochem Behav* Jan. 1995;50(1):49–54.

Lemaire I, Yang H, Cantin MF, Lemaire S., "Up–regulation of cytokine production in alveolar macrophages by histogranin, a novel endogenous pentadecapetide.", *Immunol Lett* Jun. 1994;41(1):37–42.

Dumot M, Prasad J, Lemaire S., "Interaction of histogranin and related peptides with [3H]dextromethorphan binding sites in rat brain.", *Neurosci Lett*, May 23, 1994;173(1–2):135–8.

Rogers C, Lemaire S. J, "Characterization of [125I][Ser1] histogranin binding sites in rat brain.", *Pharmacol Exp Ther* Oct. 1993;267(1);350–6.

Lemaire S, Griffiths J, Lapierre C, Lemaire I, Merali Z, Ravindran AV., "Characterization of histogranin receptors in human peripheral blood lymphocytes.", *Biochem Biophys Res Commun* Aug. 1, 1993;194(3): 1323–9.

Lemaire S, Shukla VK, Rogers C, Ibrahim IH, Lapierre C, Parent P, Dumont M., "Isolation and characterization of histogranin, a natural peptide with NMDA receptor antagonist activity.", *Eur J. Pharmacol* May 15, 1993:245 (3):247–56.

Hong Ruan., Abstract of Dissertation submitted to The University of Ottawa for M.Sc. , "The antinociceptive effects of HN and related peptides in the mouse writhing and tailflck tests: the possible role of central D2 Receptor", Aug., 1999.

Yamaki S. et al. High performance liquid chromatography of peptides on a microspherical carbon column; *J. of chromatography A* 729:143–153 (1996).

* cited by examiner

SEQUENCE LISTING

```
<160> NUMBER OF SEQ ID NOS: 22

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 1

Arg Gln Gly Arg
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 2

Gly Gln Gly Arg
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 3

Gly Gln Ala Arg
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:  synthetic
      peptide
```

```
<400> SEQUENCE: 4

Arg Gln Ala Arg
 1

<210> SEQ ID NO 5
<211> LENGTH: 4
<212> TYPE: PRT
<213> ORGANISM: Artificial Sequence
<220> FEATURE:
<221> NAME/KEY: NON_TER
<222> LOCATION: (1)..(4)
<223> OTHER INFORMATION: cyclic peptide
<223> OTHER INFORMATION: Description of Artificial Sequence:  synthetic
      peptide

<400> SEQUENCE: 5

Gly Gln Ala Arg
 1

<210> SEQ ID NO 6
<211> LENGTH: 4
<212> TYPE: PRT
<213> ORGANISM: Artificial Sequence
<220> FEATURE:
<221> NAME/KEY: NON_TER
<222> LOCATION: (1)..(4)
<223> OTHER INFORMATION: cyclic peptide
<223> OTHER INFORMATION: Description of Artificial Sequence:  synthetic
      peptide

<400> SEQUENCE: 6

Arg Gln Ala Arg
 1

<210> SEQ ID NO 7
<211> LENGTH: 4
<212> TYPE: PRT
<213> ORGANISM: Artificial Sequence
<220> FEATURE:
<221> NAME/KEY: NON_TER
<222> LOCATION: (1)..(4)
<223> OTHER INFORMATION: cyclic peptide
<223> OTHER INFORMATION: Description of Artificial Sequence:  synthetic
      peptide

<400> SEQUENCE: 7

Gly Gln Tyr Arg
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 8

Gly Gln Tyr Arg
 1

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide
```

```
<400> SEQUENCE: 9

Arg Gln Gly Arg Thr Leu Tyr Gly Phe
  1               5

<210> SEQ ID NO 10
<211> LENGTH: 8
<212> TYPE: PRT
<213> ORGANISM: Artificial Sequence
<220> FEATURE:
<221> NAME/KEY: NON_TER
<222> LOCATION: (1)..(8)
<223> OTHER INFORMATION: cyclic peptide
<223> OTHER INFORMATION: Description of Artificial Sequence:  synthetic
      peptide

<400> SEQUENCE: 10

Gly Gln Ala Arg Gly Gln Ala Arg
  1               5

<210> SEQ ID NO 11
<211> LENGTH: 8
<212> TYPE: PRT
<213> ORGANISM: Artificial Sequence
<220> FEATURE:
<221> NAME/KEY: NON_TER
<222> LOCATION: (1)..(8)
<223> OTHER INFORMATION: cyclic peptide
<223> OTHER INFORMATION: Description of Artificial Sequence:  synthetic
      peptide

<400> SEQUENCE: 11

Arg Gln Ala Arg Arg Gln Ala Arg
  1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 12

Val Val Tyr Ala Leu Lys Arg Gln Gly Arg Thr Leu Tyr Gly Phe
  1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 13

Tyr Ala Leu Lys Arg Gln Gly Arg Thr Leu Tyr Gly Phe Gly Gly
  1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide
```

-continued

```
<400> SEQUENCE: 14

Met Asn Tyr Ala Leu Lys Gly Gln Gly Arg Thr Leu Tyr Gly Phe
  1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 15

Ser Asn Tyr Ala Leu Lys Gly Gln Gly Arg Thr Leu Tyr Gly Phe
  1               5                  10                  15

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 16

Gly Gln Gly Arg Thr Leu Tyr Gly Phe
  1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 17

Met Asn Tyr Ala Leu Lys Gly Gln Gly Arg
  1               5                  10

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Val Gln Trp Lys
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

His Asn Leu Lys
  1

<210> SEQ ID NO 20
<211> LENGTH: 4
<212> TYPE: PRT
```

```
<213> ORGANISM: Artificial Sequence
<220> FEATURE:
<221> NAME/KEY: SITE
<222> LOCATION: (2)
<223> OTHER INFORMATION: Abnormal linkage: pseudopeptide bond (CS-NH)
      between amino acids at positions 2 and 3
<223> OTHER INFORMATION: Description of Artificial Sequence: synthetic
      peptide

<400> SEQUENCE: 20

Leu Gln Leu Lys
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Lys Gln Phe Lys
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

Gly Glu Leu Lys
  1
```

HISTOGRANIN PEPTIDES AND THEIR ANALGESIC USE

FIELD OF THE INVENTION

This invention relates to novel peptides and pseudopeptides useful as analgesics.

BACKGROUND OF THE INVENTION

Chronic pain may have multiple causes including inflammation, peripheral nerve injury, cancer, AIDS, and diabetes. Treatment of chronic pain has included the administration of analgesics.

Analgesic compounds are agents which alleviate pain without causing a loss of consciousness; they may also reduce inflammation. Known analgesics have not been particularly effective in the treatment of chronic pain. For instance, aspirin derivatives and non-steroidal anti-inflammatory agents have limited efficacy and have a number of side-effects including interference with blood coagulation and the exacerbation of peptic ulcers; morphine and opioid analgesics have shown some beneficial effects, but cause side-effects such as marked tolerance, and addiction and withdrawal syndromes; and the known N-methyl-D-aspartate (NMDA) receptor antagonists are effective in certain animal models, but produce behavioural side-effects including motor impairment, learning impairment, and ataxia.

U.S. Pat. No. 5,656,267 (Aug. 12, 1997) describes a method of alleviating chronic pain involving the transplantation of cells into a region of the central nervous system of patients suffering from chronic pain. However, this method is not practical.

SUMMARY OF THE INVENTION

In one aspect the invention provides novel linear peptides and pseudopeptides, having analgesic properties, of Formula I:

Formula I

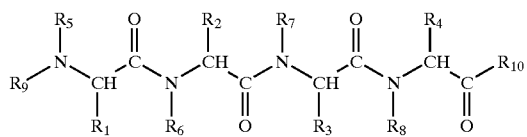

wherein $R_1$ represents hydrogen, alkyl, alkenyl, alkynyl, —$(CH_2)_n$—$NH_2$, —$(CH_2)_n$—NH—C(=NH)$NH_2$, or

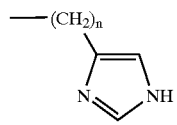

wherein "n" is an integer from 0 to 10;

$R_2$ represents —$(CH_2)_n CONH_2$, wherein "n" represents an integer from 0 to 10;

$R_3$ represents hydrogen, alkyl, alkenyl, alkynyl, the radical of formula:

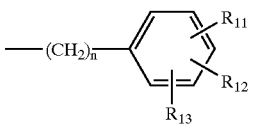

or the radical of formula:

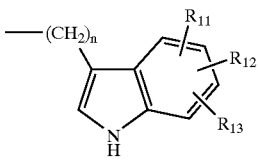

wherein

"n" represents an integer from 0 to 10; and $R_{11}$, $R_{12}$ and $R_{13}$ may be the same or different and represent hydrogen, alkyl, alkenyl, alkynyl, —I, —F, —Br, —Cl, or —OH; and $R_4$ represents —$(CH_2)_n NH_2$, —$(CH_2)_n NHC(=NH)NH_2$, or

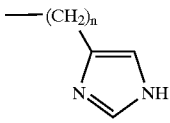

wherein "n" represents an integer from 0 to 10;

$R_5$ and $R_9$ may be the same or different and represent hydrogen, alkyl, alkenyl, alkynyl, alkylcarbonyl, aminocarbonyl, alkylaminocarbonyl, dialkylaminocarbonyl, dialkylamino, or —$(CH_2)_n$aryl, wherein "n" is an integer from 1 to 10;

$R_6$, $R_7$, and $R_8$ may be the same or different and represent hydrogen, alkyl, alkenyl, or alkynyl;

$R_{10}$ represents hydroxy, alkoxy, alkenyloxy, alkynyloxy, amino, alkylamino, dialkylamino, alkylaryl, arylalkoxy, aryloxy, alkoxyaryl, $A_1$, $A_1$-$A_2$, $A_1$-$A_2$-$A_3$, $A_1$-$A_2$-$A_3$-$A_4$, or $A_1$-$A_2$-$A_3$-$A_4$-$A_5$, wherein $A_1$ represents threonine or serine;

$A_2$ represents leucine, glycine, alanine, valine, or isoleucine;

$A_3$ represents tyrosine, phenylalanine, or tryptophan;

$A_4$ represents glycine, alanine, leucine, isoleucine, or valine; and $A_5$ represents phenylalanine, tyrosine, or tryptophan; pseudopeptide analogues thereof wherein one or more of the carbonyl groups of the peptide linkage is replaced by —C(=S)— or by —$CH_2$—, and/or wherein one or more of the amide bonds, —C(O)—NH—, is replaced by the retro-verso form, —NH—C(O)—, thereof; and pharmaceutically acceptable salts and esters thereof.

In another aspect, the invention provides novel cyclic peptides and cyclic pseudopeptides, having analgesic properties, of Formula II:

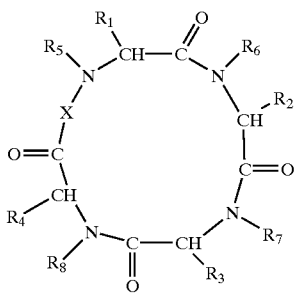

Formula II wherein $R_1$, $R_2$, $R_3$, $R_4$, $R_5$, $R_6$, $R_7$, and $R_8$, are as defined above; and X represents an amino acid or peptide fragment represented by $A_1$, $A_1$-$A_2$, $A_1$-$A_2$-$A_3$, $A_1$-$A_2$-$A_3$-$A_4$, or $A_1$-$A_2$-$A_3$-$A_4$-$A_5$, wherein $A_1$, $A_2$, $A_3$, $A_4$, and $A_5$ are as defined above; or a divalent group of formula:

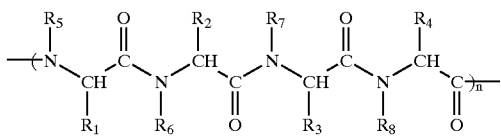

wherein

"n" represents an integer from 0 to 10; and $R_1$, $R_2$, $R_3$, $R_4$, $R_5$, $R_6$, $R_7$, and $R_8$ are as defined above; pseudopeptide analogues thereof wherein one or more of the carbonyl groups of the peptide linkage is replaced by —C(=S)— or by —CH$_2$—, and/or wherein one or more of the amide bonds, —C(O)—NH—, is replaced by the retro-verso form, —NH—C(O)—, thereof; and pharmaceutically acceptable salts and esters thereof.

In another aspect, the invention provides a pharmaceutical composition for the treatment of pain, especially chronic pain, comprising a peptide or pseudopeptide of the invention in admixture with a suitable pharmaceutically acceptable diluent or carrier.

In a further aspect, the invention provides use of a peptide or pseudopeptide of the invention for the treatment of pain, especially chronic pain.

In another aspect, the invention provides use of a peptide or pseudopeptide of the invention for the manufacture of a medicament for the treatment of pain, especially chronic pain.

The invention also provides a commercial package which contains the peptide or pseudopeptide of the invention together with instructions for the use thereof, for the treatment of pain.

DESCRIPTION OF PREFERRED EMBODIMENTS OF THE INVENTION

Normally, the peptides of this invention will be based upon L-amino acids, and amino acids should be understood to be L-amino acids, unless otherwise indicated or unless the context requires otherwise. However, in certain instances, it may be advantageous to utilize the D-form of the acids. Accordingly, both forms are within the scope of this invention.

The preferred forms for the amino acids comprised within Formulae I and II are the levo (L) forms for amino acids with $R_1$ and $R_3$ side-chains and dextro (D) forms for amino acids with $R_2$ and $R_4$ side-chains.

As alkyl groups, we mention ones with up to 10 carbons, preferably up to 4 carbons, which can be straight or branched and can have from 0 to 4 carbon-carbon double and/or triple bonds. Examples include methyl, ethyl, n-propyl, isopropyl, n-butyl, isobutyl, sec-butyl, and 2-ethyl-hexyl. As alkoxy groups we mention groups with up to 10 carbon atoms, preferably up to 4 carbon atoms. Examples of alkoxy groups include methoxy, ethoxy, propoxy, and tert-butoxy. As aryl groups, we mention 5- and 6-membered single-ring aromatic radicals which include from zero to four heteroatoms selected from nitrogen, oxygen, and sulfur, and the corresponding benzo-fused groups. Examples include phenyl, thienyl, furanyl, pyridinyl, imidazolyl, pyrimidyl, isoxazolyl, thiazolyl, triazolyl, tetrazolyl, pyrrolyl, naphthyl, indolyl, and quinolyl.

Preferred peptides and pseudopeptides according to Formula I have the following Formula III:

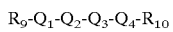

wherein $Q_1$ represents glycine, alanine, valine, leucine, isoleucine, lysine, histidine, or arginine;

$Q_2$ represents asparagine or glutamine;

$Q_3$ represents glycine, alanine, valine, leucine, isoleucine, phenylalanine, tryptophan, or tyrosine;

$Q_4$ represents lysine, arginine, or histidine;

$R_9$ represents hydrogen; and $R_{10}$ represents hydroxy;

pseudopeptide analogues thereof wherein one or more of the carbonyl groups of the peptide linkage is replaced by —C(=S)— or by —CH$_2$—, and/or wherein one or more of the amide bonds, —C(O)—NH—, is replaced by the retro-verso form, —NH—C(O)—, thereof; and pharmaceutically acceptable salts and esters thereof.

More preferred peptides and pseudopeptides are represented by Formula III wherein $Q_1$ represents glycine or arginine;

$Q_2$ represents L-glutamine or D-glutamine;

$Q_3$ represents glycine, alanine, or tyrosine;

$Q_4$ represents L-arginine or D-arginine;

$R_9$ represents hydrogen; and $R_{10}$ represents hydroxy;

pseudopeptide analogues thereof wherein one or more of the carbonyl groups of the peptide linkage is replaced by —C(=S)— or by —CH$_2$—, and/or wherein one or more of the amide bonds, —C(O)—NH—, is replaced by the retro-verso form, —NH—C(O)—, pharmaceutically acceptable salts and esters thereof.

Preferred cyclic peptides and pseudopeptides have the following Formula IV:

Formula IV

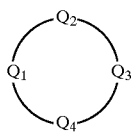

wherein

Q₁ represents glycine, alanine, valine, leucine, isoleucine, lysine, histidine, or arginine;

Q₂ represents asparagine or glutamine;

Q₃ represents glycine, alanine, valine, leucine, isoleucine, phenylalamine, tryptophan, or tyrosine; and Q₄ represents lysine, arginine, or histidine;

pseudopeptide analogues thereof wherein one or more of the carbonyl groups of the peptide linkage is replaced by —C(=S)— or by —CH₂—, and/or wherein one or more of the amide bonds, —C(O)—NH—, is replaced by the retro-verso form, —NH—C(O)—, thereof; and pharmaceutically acceptable salts and esters thereof.

More preferred peptides and pseudopeptides are represented by Formula IV
wherein Q₁ represents glycine or arginine;

Q₂ represents L-glutamine or D-glutamine;

Q₃ represents glycine, alanine, or tyrosine;

Q₄ represents L-arginine or D-arginine;

pseudopeptide analogues thereof wherein one or more of the carbonyl groups of the peptide linkage is replaced by —C(=S)— or by —CH₂—, and/or wherein one or more of the amide bonds, —C(O)—NH—, is replaced by the retro-verso form, —NH—C(O)—, thereof; and pharmaceutically acceptable salts and esters thereof.

Specific compounds of the invention include the following:

Especially preferred are peptides 8 and 9.

The linear peptides can be synthesized by solid-phase procedures known in the art (see for example: Merrifield, J. Am. Chem. Soc. 85, 2149, 1963 and Prasad et al., Can. J. Physiol. Pharmacol. 73, 209, 1995, the disclosures of which are incorporated by reference).

Cyclic peptides can be synthesized using the Kaiser's oxime-resin procedure known in the art (see for example: Osapay et al., Tetrahedron Letters, 31, 6121–6124, and Nishino et al, J. Chem. Soc. Kin. Trans. 1, 939–946, 1986, the disclosures of which are incorporated by reference).

The CO—NH bond of the peptides can be replaced by CO—N-alkyl by procedures known in the art (see for example: Tachibana et al., Design and synthesis of metabolically stable analogues of dynorphin-A and their analgesic characterisitics in "Biowarning systems in the brain" Ed. H. Takagi, Y. Oomoro, M. Ito, and H. Otsuka. University of Tokyo Press, Tokyo, 1988, the disclosure of which is herein incorporated by reference).

The amide bond or bonds, —C(O)—NH—, of the peptide linkage may be replaced by retro-verso forms, —NH—C(O)—, thereof. The synthesis is performed as for linear peptides except that retro-verso forms of the peptides are introduced in place of the normal peptide linkages. For example, the Gly-Gln bound in Gly←Gln→Ala→Arg can be obtained by introducing:

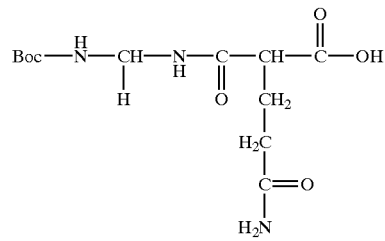

in solid-phase synthesis. The product is a mixture of 4 racemers that are separated and isolated by HPLC.

To prepare pseudopeptides wherein one or more of the carbonyl groups of the peptide linkage is replaced by

```
Peptide 1    H-Arg-Gln-Gly-Arg-OH                          (SEQ ID NO:1)

Peptide 2    H-Gly-Gln-Gly-Arg-OH                          (SEQ ID NO:2)

Peptide 3    H-Gly-Gln-Ala-Arg-OH                          (SEQ ID NO:3)

Peptide 4    H-Arg-Gln-Ala-Arg-OH                          (SEQ ID NO:4)

Peptide 5    cyclic(-Gly-Gln-Ala-Arg-)                     (SEQ ID NO:5)

Peptide 5B   cyclic(-Gly-Gln-Ala-Arg-Gly-Gln-Ala-Arg-)     (SEQ ID NO:10)

Peptide 6    cyclic(-Arg-Gln-Ala-Arg-)                     (SEQ ID NO:6)

Peptide 6B   cyclic(-Arg-Gln-Ala-Arg-Arg-Gln-Ala-Arg-)     (SEQ ID NO:11)

Peptide 7    cyclic(-Gly-Gln-Tyr-Arg-)                     (SEQ ID NO:7)

Peptide 8    cyclic(-Gly-Gln-Tyr-D-Arg-)

Peptide 9    cyclic(-Gly-D-Gln-Tyr-D-Arg-)

Peptide 10   H-Gly-Gln-Tyr-Arg-OH                          (SEQ ID NO:8)

Peptide 11   H-Gly-Gln-Tyr-D-Arg-OH

Peptide 12   H-Gly-D-Gln-Tyr-D-Arg-OH

Peptide 13   H-Arg-Gln-Gly-Arg-Thr-Leu-Tyr-Gly-Phe-OH      (SEQ ID NO:9)
```

—C(=S)— or by —CH$_2$— pseudopeptide bonds ψ(CS—NH) or ψ(CH2-NH) can be introduced into the peptides described, as given, for example, by Michelot et al (Solid-phase synthesis of endothiopeptides using 3-(N-Boc-aminothioacyl)-1,3-thiazolidine-2-thiones: new efficient thioacylating reagents in "Innovation and perspectives in solid-phase synthesis, biological and biomedical applications" Ed. R. Epton, Mayflower Worldwide Inc., Birmingham, 1996) or as described by Sasaki and Coy (Peptides 8, 119–121, 1987), respectively, the disclosures of both of which are incorporated by reference The peptides and pseudopeptides of the invention may be formed into acid addition, base addition, metallic, and zwitter-ionic salts. Such salts are within the scope of this invention. For administration the salts must of course be pharmaceutically acceptable, but other salts may be of value as intermediates in synthesis or in purification. Representative acid addition salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, benzene-sulphonate, mesylate, glucoheptonate, lactobionate, and laurylsulphonate salts and the like; representative organic amines useful for the formation of base addition salts and quaternary ammonium salts include aliphatic and cyclic amides, for example, ethylamine, diethylamine, ethylenediamine, ethanolamine, diethanolamine, piperazine, guanidinium and the like; representative metal salts include the lithium, sodium, potassium, calcium, magnesium, silver and aluminum salts, and the like. All these salts can be prepared by methods well known to those skilled in the art.

Preferred esters are those that will undergo hydrolysis in vitro to the free acid, for example esters of choline, cholesterol, and salicylic acid. Hence the esters can be regarded as pro-drugs of the compounds of the invention.

Referring to X of Formula II, when n represents zero, X is a direct covalent bond.

The invention extends to pro-drugs and to metabolites of the compounds of formula I and II.

Pharmaceutically-acceptable compositions which comprise a therapeutically-effective amount of one or more of the compounds of Formula I or II, as described hereinabove, together with one or more pharmaceutically-acceptable carriers and/or diluents are included in this invention.

Compositions of the present invention may conveniently be presented in unit dosage form and may be prepared by any methods well known in the art of pharmacy. The amount of active ingredient (compounds of Formula I and II) which can be combined with a carrier material to produce a single dosage form will vary depending upon numerous factors such as the host being treated and the particular mode of administration. The amount of active ingredient to be combined with a carrier material to produce a single dosage form will be that amount of the compound which produces a therapeutic effect. Generally, the amount of the compound of the invention will be in the range from about 1 percent to about ninety-nine percent of the composition, preferably about 5 percent to about 70 percent, most preferably from about 10 to about 30 percent although the amount of the dose and the mode of administration will be determined by the doctor or other medical professional.

An appropriate dose may be 5–50 mg per person per day, although the appropriate dose will, of course, be determined by the clinician.

Suitable methods of administration of the compounds of this invention, and the compositions formed therewith include oral, nasal, topical (including buccal and sublingual), rectal, vaginal and/or parenteral administration, including injectable.

EXAMPLES

1) Synthesis of Linear Peptides

Synthesis of linear peptides was performed as previously described (Prasad et al., Can. J. Physiol. Pharmacol. 73:209–214, 1995, herein incorporated by reference) by the use of pre-formed symmetrical anhydrides of Boc-amino acids with the solid-phase method (Merrifield, J. Am. Chem. Soc. 85:2149–2154, 1963, herein incorporated by reference) and chloromethylated copolystyrene-divinylbenzene 1% crosslinkage (0.75 mequiv. Cl/g) as the resin.
Peptide 3:

H-Gly-Gln-Ala-Arg-OH (SEQ ID NO:3)

The C-terminal amino acid (Boc(Tos)-Arg) was esterified to the resin according to the procedure of Gisin (Helv. Chim. Acta, 56:1476–1482, 1973, herein incorporated by reference) with a final yield of 0.3 mmol/g resin. Thereafter, Boc-Ala, Boc-Gln and Boc-Gly were attached consecutively according to the following coupling cycle: i) one wash with CH$_2$Cl$_2$, ii) one prewash with 40% TFA in CH$_2$Cl$_2$, iii) 20 min deprotection with 40% TFA in CH$_2$Cl$_2$, iv) three washes (one with CH$_2$Cl$_2$, one with 50% dioxane in CH$_2$Cl$_2$ and one with CH$_2$Cl$_2$, v) prewash with 5% DEA, vi) 5 min neutralization with 5% DEA, vii) three washes with CH$_2$Cl$_2$, viii) one hour coupling with pre-formed symmetrical anhydrides of Boc-amino acids (six equiv. as compared with the resin substitution of 0.3 mol/g), ix) three washes with CH$_2$Cl$_2$, x) two washes with isopropano.

The peptide was cleaved from the resin and deprotected with liquid HF at 0° C. in the presence of anizole (10%, v/v). HF was removed in vacuo, and the residue was washed with ether before extraction of the peptide with 25% acetic acid followed by lyophilization. The peptide was then purified by passage through Sephadex™ G-10 resin (2×25 cm column) and HPLC on a Bio-Sil™ C18 column (Waters, Milford, Mass.). The product was eluted from the HLPC column with a gradient of acetonitrile (0–30% in 0.1% TFA), detected by UV at 240 nm and lyophilized to yield 20–25% of the pure compound (based on the starting Boc-amino acid resin). The purity of the peptide was verified by thin layer chromatography on silica gel plates (layer thickness 0.25 mm) BDH Chemicals Associate of E. Merck, Darmstadt, Germany) (one spot, R$_f$: 0.19; nBuOH:EtOH;HOAc:H$_2$O, 1:1:1:1). Amino acid analysis of an acid digest gave: Glu, 0.99; Arg, 1.02; Gly, 0.96 and Ala, 1.03.

The title compound was obtained as a white powder. The molecular formula is C$_{16}$H$_{30}$N$_8$O$_6$. Mol Wt/MS-ESI: 430.23 (M+H: 431). Percentage purity based on HPLC was 95%–98%. Soluble in water and DMSO.

The following linear peptides were synthesized based on the method given above for peptide 3:
Peptide 1:

H-Arg-Gln-Gly-Arg-OH (SEQ ID NO:1)

The title compound was obtained as a white powder. The molecular formula is C$_{19}$H$_{37}$N$_{11}$O$_6$. Mol Wt/MS-ESI: 515.29 (M+H: 516). Percentage purity based on HPLC was 95%–98%. The compound was soluble in water and DMSO.
Peptide 2:

H-Gly-Gln-Gly-Arg-OH (SEQ ID NO:2)

The title compound was obtained as a white powder. The molecular formula is —C$_{15}$H$_{28}$N$_8$O$_6$. Mol Wt/MS-ESI: 416.21 (M+H: 417). Percentage purity based on HPLC was 95%–98%. Soluble in water and DMSO.

Peptide 4:
H-Arg-Gln-Ala-Arg-OH (SEQ ID No:4)
The title compound was obtained as a white powder. The molecular formula is $C_{20}H_{39}N_{11}O_6$. Mol Wt/MS-ESI: 529.31 (M+H: 530). Percentage purity based on HPLC was 95%–98%. Soluble in water and DMSO.

Peptide 10:
H-Gly-Gln-Tyr-Arg-OH (SEQ ID NO:8)

Peptide 11:
H-Gly-Gln-Tyr-D-Arg-OH

Peptide 12:
H-Gly-D-Gln-Tyr-D-Arg-OH

Peptide 13:
H-Arg-Gln-Gly-Arg-Thr-Leu-Tyr-Gly-Phe-OH (SEQ ID NO:9).

2) Synthesis of Cyclic Peptides

Peptide 8:

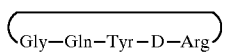

Boc-Gly-Oxime-Resin was prepared by mixing oxime-resin (Novabiochem, 1.5 g 0.57 meq/g) with Boc-Gly (1.3 g, 9 eq) in the presence of N'N-dicyclohexylcarbodiimide (DCC) (9.9 ml of DCC 8%, 4.5 eq), 4-dimethylaminopyridine (DMAP) (0.3 g, 3 eq), 1-hydroxybenzotriazole hydrate (HOBt) (0.4 g, 3 eq) in dichloromethane (DCM) at room temperature for 12 hours. The resin was subjected to two washes with DCM, one wash with 2-propanol and one wash with DCM. The free oxime groups were capped by acetylation with acetic anhydride (0.4 ml, 5 eq) for 30 minutes. The peptide chain was then assembled according to the following coupling steps: (i) one wash with 25% trifluoroacetic acid in DCM (TFA-DCM); (ii) deprotection with 25% TFA-DCM (30 min); (iii) two washes with DCM; (iv) one wash with 2-propanol; (v) three washes with DCM; (vi) one wash with dimethylformamide (DMF); (viii) coupling of Boc-D-Arg(Tos)-OH (1.1 g, 3 eq) in presence of benzotriazole-yl-oxy-tris-pyrrolidino-phosphonium hexafluorophosphate (PyBOP), (1.3 g, 3 eq), HOBt (0.13 g, 1 eq) and diisopropylethylamine (DIEA) (0.95 ml, 6.5 eq) in DMF (45 min.). In cycles 2 and 3, step viii is performed with Boc-Tyr(2,6-di-Cl-Bzl)—OH (1.1 g, 3 eq) and Boc-D-Gln (0.6 g, 3 eq), respectively; (ix) three washes with DMF; (x) two washes with DCM. Solvent volumes were 15 ml/g resin. Coupling efficiency was checked at each coupling cycle by the Kaiser test (Kaiser et al., Anal. Biochem., 34, 595–598, 1970, the disclosure of which is incorporated by reference). The peptide was cleaved from the resin by intrachain aminolysis in the presence of AcOH (0.097 ml, 2 eq) and DIEA (0.293 ml, 2 eq) in 30 ml DMF at room temperature for 24 hours. The product was obtained from solution phase by filtration. Protecting groups were removed with anhydrous hydrogen fluoride (HF) at 0° C. for 30 minutes. The crude product was purified by Sephadex™ G-10, then RP-HPLC (Bondapak $C_{18}$ column, 10 μm×125A, 25×100 mm), with a gradient of 0–50% water-acetonitrile, 0.1% TFA over 65 minutes. The final yield was 22 mg (p5%) based on starting resin. The purity and identity of the synthetic peptide was assessed by analytical HPLC on Bondapak C18 column, 10 μm×125A, 3.9×300 mm with a gradient of 0–50% water-acetonitrile, 0.1% TFA over 50 minutes, k':2.7, molecular mass by FAB-MS: 505 (calcd: 504.24), amino acid analysis: D-A-g (1.1), Gln (1.0), Gly (1.0), Tyr (1.0). The following cyclic peptides were synthesized based on the method given above for peptide 8.

Peptide 5:

(SEQ ID NO:5)

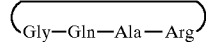

The title compound was obtained as a white powder. The molecular formula is $C_{16}H_{28}N_8O_5$. Mol Wt/MS-ESI: 824.44 (M+H: 413). Percentage purity based on HPLC was 95%–98%. Soluble in water and DMSO. K' (HPLC): 2.25. Rf (B:A:W:P/15:3:10:12)=0.75.

Peptide 5B:

(SEQ ID NO:10)

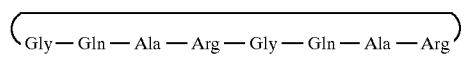

The title compound was obtained as a white powder. The molecular formula is $C_{32}H_{56}N_{16}O_{10}$. Mol Wt/MS-ESI: 824.44 (M+H: 825). Percentage purity based on HPLC was 98%. Soluble in water and DMSO.

Peptide 6:

(SEQ ID NO:6)

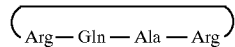

The title compound was obtained as a white powder. The molecular formula is $C_{20}H_{37}N_{11}O_5$. Mol Wt/MS-ESI: 511.58 (M+H: 512). Percentage purity based on HPLC was 95%–98%. Soluble in water and DMSO. K' (HPLC): 2.17. Rf (B:A:W:P/15:3:10:12)=0.79.

Peptide 6B:

(SEQ ID NO:11)

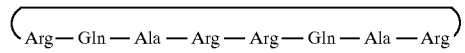

The title com pound was obtained as a white powder. The molecular formula is $C_{40}H_7N_{22}O_{10}$. Mol Wt/MS-ESI: 1023.12. Percentage purity based on HPLC was 95%. Soluble in water and DMSO. K' (HPLC): 2.23. Rf (B:A:W:P/15:3:10:12)=0.85

Peptide 7:

(SEQ ID NO:7)

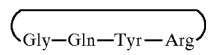

The title compound was obtained as a white powder. The molecular formula is $C_{22}H_{32}N_8O_6$. Mol Wt/MS-ESI: 504.24 (M+H: 505). Percentage purity based on HPLC was 95%–98%. Soluble in water and DMSO. K' (HPLC): 2.7. Rf (B:A:W:P/15:3:10:12)=0.49.

Peptide 9:

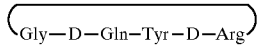

The title compound was obtained as a white powder. The molecular formula is $C_{22}H_{32}N_8O_6$. Mol Wt/MS-ESI: 504.24 (M+H: 505). Soluble in water and DMSO. K' (HPLC): 2.7. Rf (B:A:W:P/15:3:10:12)=0.47.

3) Administration of the Peptides

Mice (male 20–25 g, Swiss Webster) were obtained from Charles River (Canadian Breeding Farm, St. Constant, Quebec). They were housed five per cage in a room with controlled temperature (22±2° C.), humidity and artificial light (06.30–19 h). The animals had free access to food and water and were used after a minimum of 4 days of acclimatisation to housing conditions. Experiments were carried out between 10:00 a.m. and 4:00 p.m. in an air-regulated and soundproof laboratory (23±1° C., 40% humidity), in which mice were habituated at least 30 min before each experiment. The experiments were authorized by the animal care committee of the University of Ottawa in accordance withe the guidelines of the Canadian Council on Animal Care.

The i.c.v. administrations of the peptides were performed as described by Shukla et al. (Shukla et al., Brain Res. 591, 176, 1992 the disclosure of which is incorporated by reference). Peptides were dissolved in double-distilled sterile water (vehicle) and 10 µl of the peptide solution or vehicle was delivered gradually within approximately 3 sec. The mice exhibited normal behaviour within 1 min after injection. The administration site was confirmed by injecting Indian ink in preliminary experiments.

4) Antinociceptive Assay

Mouse Writhing Test: Antinociceptive activity of the peptides was evaluated using the acetic acid-induced writhing test according to a modification (Shukla et al. Brain Research 591, 176, 1992 the disclosure of which is incorporated by reference) of the method of Hayashi and Takemori (Eur.J. Pharmacol. 16 63, 1971 the disclosure of which is incorporated by reference). Male Swiss Webster [(SW)f BR] mice were injected intraperitoneally (i.p.) with 1.0% acetic acid (10 ml/kg) 5 min after i.c.v. injection of 0 (saline), 0.5, 1, 10, 25, 50, 75, or 100 nmol of the peptides. The number of writhes displayed by each mouse was counted for a period of 10 min after the injection of the acetic acid solution. An abdominal stretch is characterized by the contraction of the abdominal muscles, the arching of the back vent-ally such that the abdomen touches the bedding surface and the extension of one or both hind limbs. Mice were used once and then killed immediately. Groups of 10 mice were used for each dose.

The analgesic activity of the peptides was assessed in terms of either 1) the number of mice out of ten in which a given dose of a peptide is considered to be active, expressed as a percentage, or 2) the percent analgesia displayed by a test group of 10 mice.

In the first case (method #1), the compound is said to be active at a given dose if, after its administration, the number of writhes elicited by a mouse injected with acetic acid is equal to, or less than, one half the median number of writhes recorded for the saline-treated control group of mice that day, as described by Taber (Adv. Biochem. Psycholpharmacol. 8:191, 1974, the disclosure of which is incorporated by reference). The $ED_{50}$ value (the dose of the peptide that produced analgesia in 50% of the animals) with 95% confidence limits (95% CL) and potency ratios with 95% CL were measured by the method of Lichfield and Wilcox on (J. Pharmacol. Exp. Ther. 96 99, 1949, the disclosure of which is incorporated by reference) using procedure 47 of the computer program of Tallarida and Murray (in "Manual of pharmacological calculations with computer programs", 2nd ed., Springer, New York, 1987, the disclosure of which is incorporated by reference).

In the second case (method #2), the percentage of analgesia is calculated for each dose by the formula: [(mean number of writhes in control group—mean number of writhes for the test group)/(mean number of writhes in control group)×100]. The doses producing 50% analgesia ($AD_{50}$) with 95% confidence limits (95% CL) and potency ratios with 95% CL are measured by the method of Lichfield and Wilcoxon (J. Pharmacol. Exp. Ther 96, 99, 1949 the disclosure in which is incorporated by reference) using procedure 47 of the computer program of Tallarida and Murray (in "Manual of pharmacological calculations with computer programs". 2nd ed., Springer, New York, 1987, the disclosure in which is incorporated by reference).

In order to determine the length of action of the peptides of the invention, the acetic acid solution was administered at different times after the administration of the peptide, as indicated. For verifying the blockade of the analgesic effect of the peptides with receptor antagonists, naloxone (1 nmol), MK-801 (0.3 nmol) or CPP (0.1 nmol) were administered i.c.v. in an aliquot of 10 µl, alone or in combination with the peptides of the invention (50 nmol). Naloxone is an opioid antagonist. MK-801 ((+)-5-methyl-10,11-dihydro-5H-dibenzo[a,d]cyclohepten-5,10-imine maleate) and CPP ((±) 3-(2-carboxypiperazine-4-yl)-propyl-1-propionic acid) are non-competitive and competitive NMDA receptor antagonists, respectively. These two latter compounds were obtained from Tocris Neuramin, Essex, England. The experiments for assessment of the peripheral antinociceptive activity of the peptides were performed by i.p. administration of 5 µmol/kg of the tested compounds 10 min prior to the injection of the acetic acid solution. Data were analyzed by the Wilcoxon's paired non-parametric test. The criterion for statistical significance was P<0.05.

Mouse tail flick assay: Antinociception is also determined using the-radiant heat tail-flick technique (D'Amour and Smith, J. Pharmacol. Exp. Ther. 72, 74, 1941, the disclosure of which is herein incorporated by reference). Briefly, the latency to withdraw the tail from a focused light stimulus is determined using a photocell. The light intensity is set to give a control reading of about 3 sec. Baseline latencies are determined before experimental treatment as the mean of two trials, and a maximal latency of 12 s is used to minimize tissue damage. Post-treatment latencies are determined 5 min after i.c.v. injection. The antinociceptive effect is expressed as the percentage of the maximum possible effect, as calculated by the formula: %MPE=[(post-injection latency-baseline latency)/(cutoff latency-baseline latency)]× 100. The use of %MPEs takes into account differences in baseline latencies so that these differences do not bias the quantification of antinociception. Group %MPE means are compared using one-way ANOVAs and P≦0.05 is considered significant.

Antinociceptive Efficacy of Tested Peptides in the Mouse Writhing Test and the Mouse Tail-flick Assay Intracerebroventricular administration of certain peptides of the invention and related peptides in mice, induced doseand structure-dependent analgesic activities as assessed by their ability to inhibit writhing in response to intraperitoneal (i.p.) injection of acetic acid (1%) as given below. Certain peptides also produced potent antinociceptive effects in the mouse tail-flick assay as compared with morphine.

Besides testing certain peptides of the invention, a certain number of related peptides were tested for the purpose of comparison. Histogranin (HN) is an adrenal medullary peptide possessing N-methyl-D-Aspartate (NMDA) receptor antagonist activity and has analgesics properties. HN(7–15) is a fragment of histogranin (Rogers et al. (1993) J. Pharmacol. Exp. Ther. 267, 350–356, herein incorporated by reference). The other peptides used for purposes of comparison are related peptides. The sequences of these peptides are as given below:

HN:
   H-Met-Asn-Tyr-Ala-Leu-Lys-Gly-Gln-Gly-Arg-Thr-Leu-Tyr-Gly-Phe-OH (SEQ ID NO:14)

[Ser$^1$]HN:
   H-Ser-Asn-Tyr-Ala-Leu-Lys-Gly-Gln-Gly-Arg-Thr-Leu-Tyr-Gly-Phe-OH (SEQ ID NO:15)

HN(7–15):
   H-Gly-Gln-Gly-Arg-Thr-Leu-Tyr-Gly-Phe-OH (SEQ ID NO:16)

HN(1–10):
   H-Met-Asn-Tyr-Ala-Leu-Lys-Gly-Gln-Gly-Arg-OH (SEQ ID NO:17)

H4(86–100):
   H-Val-Val-Tyr-Ala-Leu-Lys-Arg-Gln-Gly-Arg-Thr-Leu-Tyr-Gly-Phe-OH (SEQ ID NO:12)

H4(89–102)(OGP):
   H-Tyr-Ala-Leu-Lys-Arg-Gln-Gly-Arg-Thr-Leu-Tyr-Gly-Phe-Gly-Gly-OH (SEQ ID NO:13).

Comparisons were also performed with morphine, an opioid analgesic.

The results are shown in Tables 1 and 2 and FIGS. 1 to 3, 5, and 6.

NMA receptor-mediated analgesic activity: In order to verify which raceptor was involved in the antinociceptive activity of [Ser$^1$]HN in the writhing test, the peotide was co-administered with the opioid antagonist naloxone, or the competitive or non competitive NMDA antagonists, CPP and MK-801, respectively. The results are given in FIG. 4.

6) Measurement of prostaglandin E$_2$ (PGE$_2$) release from Rat Alveolar Macrophages.

Male Wistar rats weighing 250 to 300 g were purchased from Harlan Sprague Dawley Inc. (Indianapolis). These animals Male Wistar rats weighing 250 to 300 g were purchased from Harlan Sprague Dawley Inc. (Indianapolis). These animals were derived from, a pathogen-free colony, shipped behind filter barriers, and housed in a horizontal laminar flow isolator (Johns Scientific Inc., Toronto). Bronchoalveolar calls were obtained by bronchoalveolar lavage as known in the art. Briefly, after the animals were killed, the abdominal aorta was severed and the trachea cannulated. A total volume of 48 ml of PBS (pH 7.4) in 8-ml aliquots was infused in each animal, 93% (45 ml) of which was recovered. The bronchoalveolar cells were obtained by centrifugation at 200 g at 4° C. for 5 minutes and resuspended in RPMI-1640 medium containing 0.5% dialysed FBS (Wisent Inc., St-Bruno, Quebec) and 0.8% Hepes, which will henceforth be referred to as tissue culture media. Differential cellular analysis, made from cytocentrifuged smears (4×10$^4$ cells) stained with Wright-Giemsa, indicated that the bronchoalveolar cells represent a pure population of alveolar macrophage (AM, 99%). Alveolar macrophages (0.2×10$^6$) were incubated in 0.2 ml tissue culture media for 20 h at 37° C. in a humidified 95% air-5% CO$_2$ atmosphere alone or with lipopolysaccharide (LPS)(1 μg/ml)(Sigma chemical Co., St-Louis, Mo.) in the presence and absence of one of [Ser$^1$]HN, Peptide 5, Peptide 6, Peptide 7, and Peptide 8 at various concentrations (10$^{-9}$M–10$^{-7}$M). The culture supernatants were collected, centrifuged and frozen at −80° C.

The following day, PGE$_2$ was determined in cell-free supernatants using a competitive enzymeimmunoassay (EIA) system (Biotrak, Amersham Pharmacia Biotech). The assay is based on competition between unlabelled PGE$_2$ and a fixed quantity of peroxidase-labelled PGE$_2$ for a limited number of binding sites on a PGE$_2$ specific antibody. It was performed according to the manufacturer's instruction. Results are expressed as percent (%) of LPS response and represent the mean±SEM of at least 3 experiments measured in triplicate.

Inhibition o prostaglandin E2 production by macrophages in response to LPS: The effect of certain peptides of the invention and related peptides on the production of PGE$_2$ by macrophages in response to LPS was tested and the results are given in FIG. 7.

BRIEF DESCRIPTION OF THE DRAWINGS

Certain results of the examples are illustrated with the aid of the Figures.

TABLE 1

Figure 1:
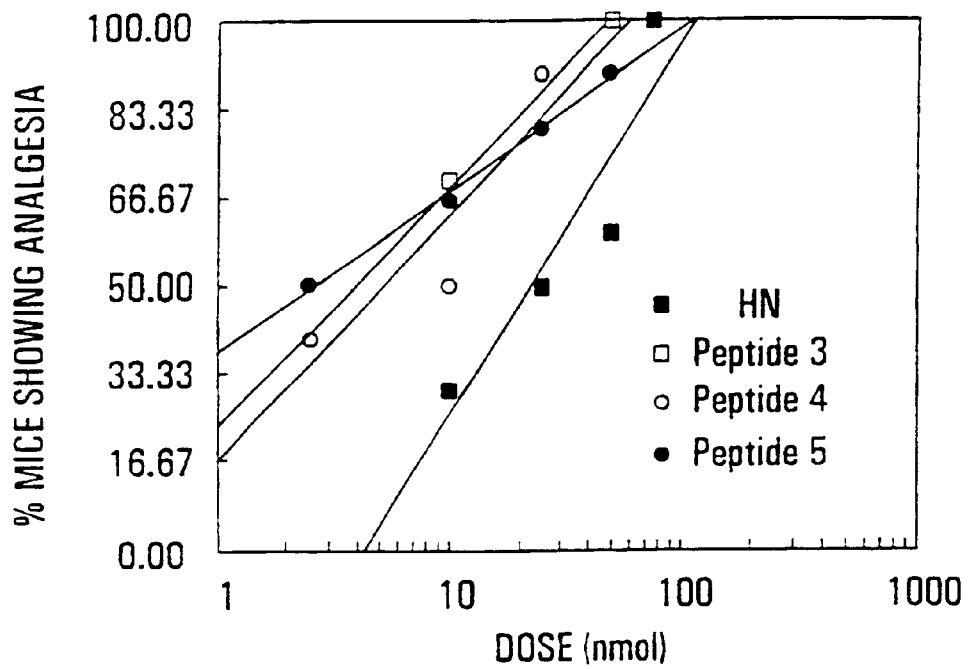
FIG. 1 gives the dose response curves of the analgesic effects of the peptides of the invention compared with several other peptides. The analgesic effect is calculated as the percent of mice showing analgesia using method #1 explained in the examples section.
Figure 2:
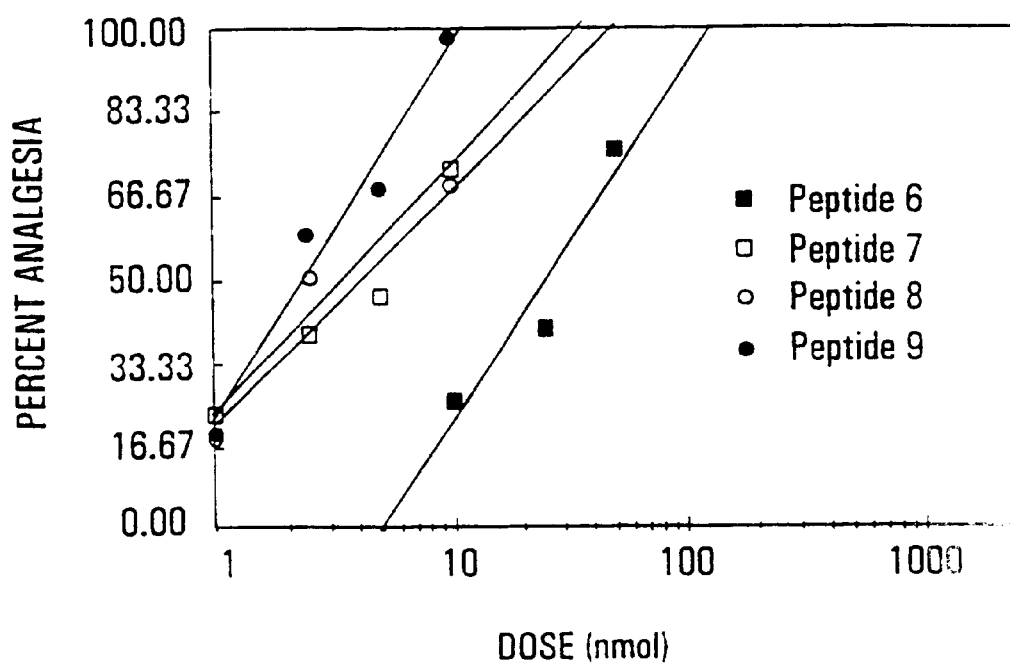
FIG. 2 gives the dose response curves of the analgesic effects of Peptide 6, Peptide 7, and Peptide 8 as calculated as percent analgesia using method #2 explained in the examples section.
Figure 3:
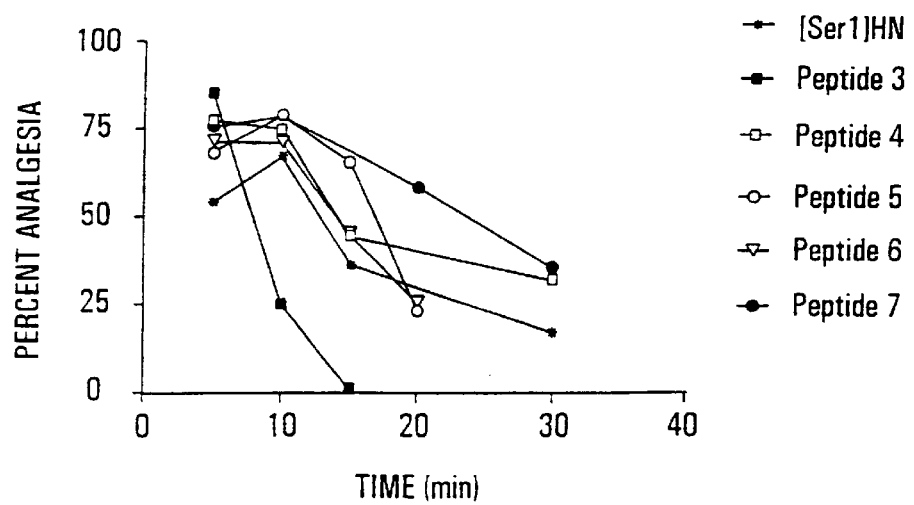
FIG. 3 gives the time response curves of the analgesic effects of [Ser$^1$]HN, Peptide 3, Peptide 5, Peptide 6, Peptide 7, and Peptide 8 measured as percent analgesia using method #2 explained in the examples section.
Figure 4:
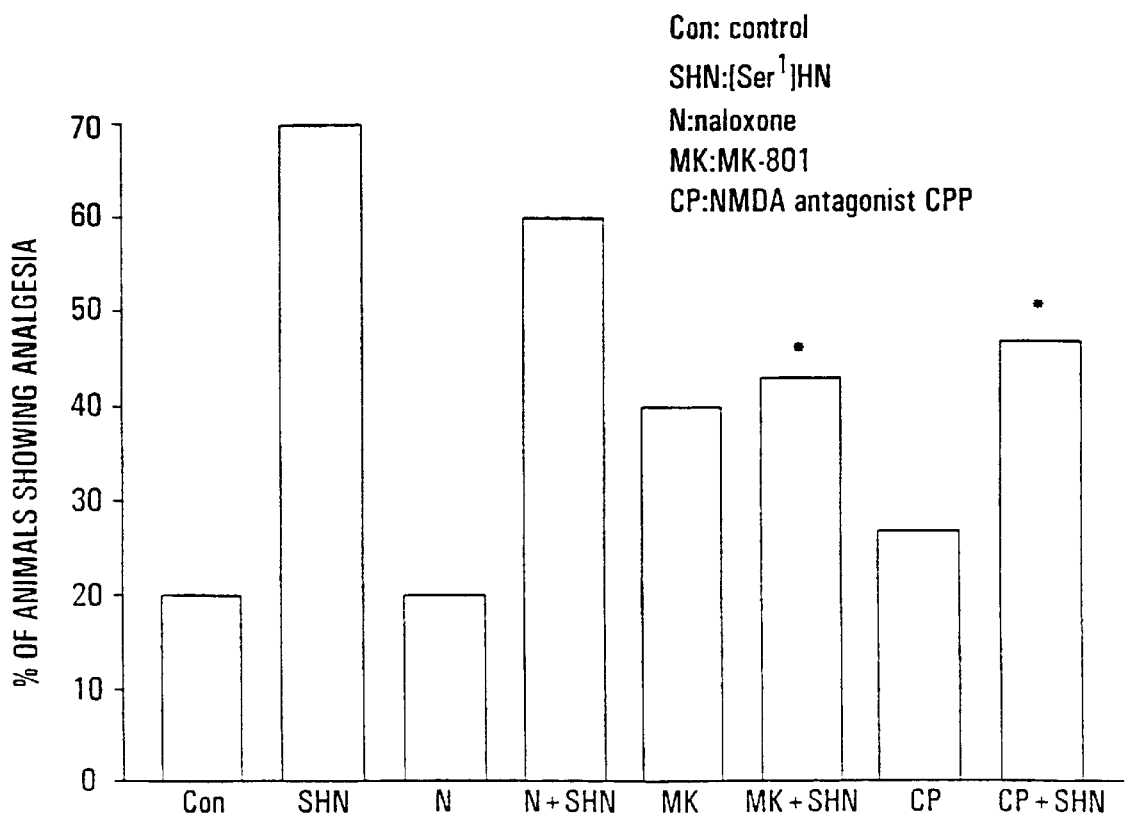
FIG. 4 shows the effects of naloxone (1 nmol, i.c.v.), MK-801 (0.1 nmol, i.c.v.) and CPP (0.3 nmol, i.c.v.) on the analgesic effects of [Ser$^1$]HN (50 nmol/mouse, i.c.v.) in the mouse writhing pain assay. *P≦0.05 as compared with [Ser$_1$]HN alone.
Figure 5:
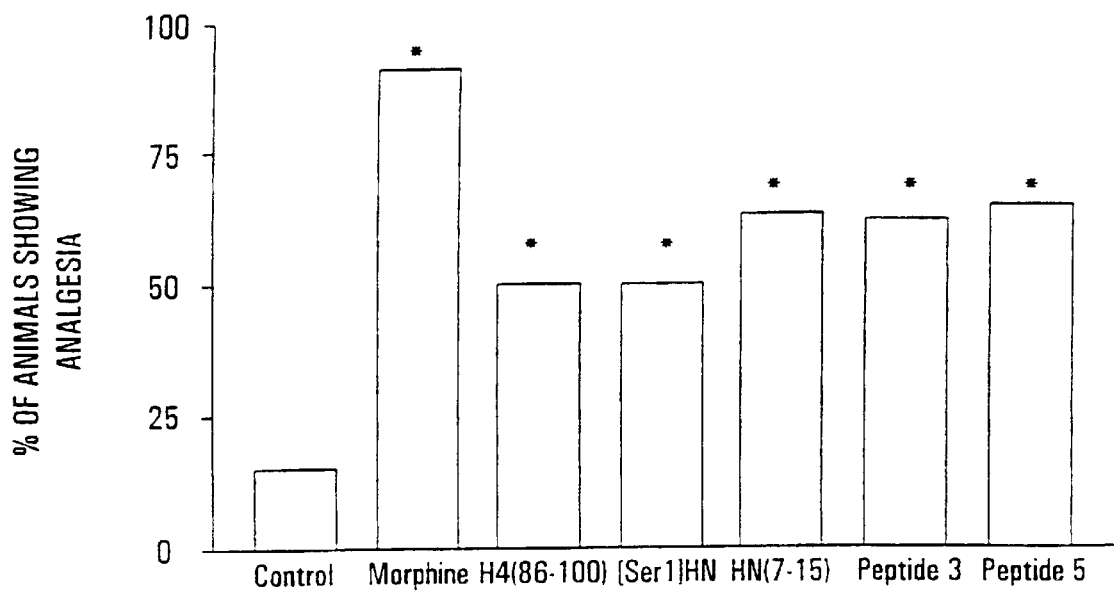
FIG. 5 shows the analgesic effects of peripheral (intraperitoneal) administration (5 μmol/kg) of morphine, histone H4(86–100), [Ser$^1$]HN, HN(7–15), Peptide 3, and Peptide 5 in the mouse writhing test. *P≦0.05 as compared with control saline.
Figure 6:
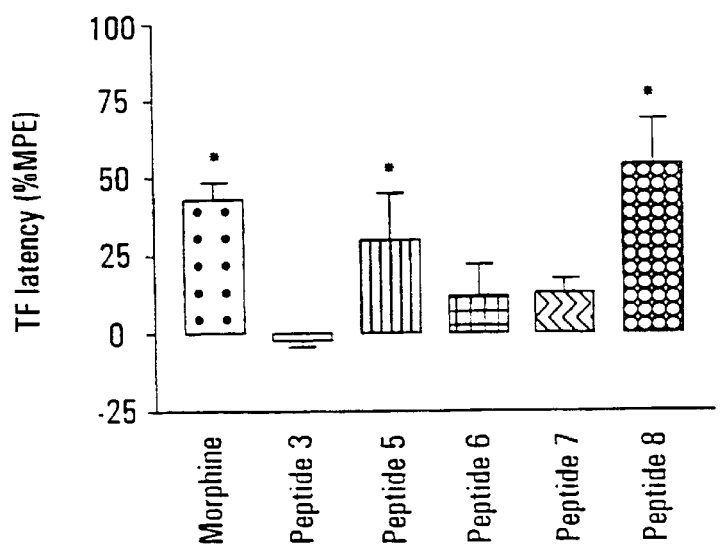
FIG. 6 shows the analgesic effects of morphine (5 μg/mouse, i.c.v.), Peptide 5 (50 nmol/mouse, i.c.v.), Peptide 6 (50 nmol/mouse, i.c.v.), Peptide 7 (10 nmol/mouse, i.c.v.) and Peptide 8 (10 nmol/mouse, i.c.v.) in the mouse tail flick assay. *P≦0.05 as compared with control saline.
Figure 7:
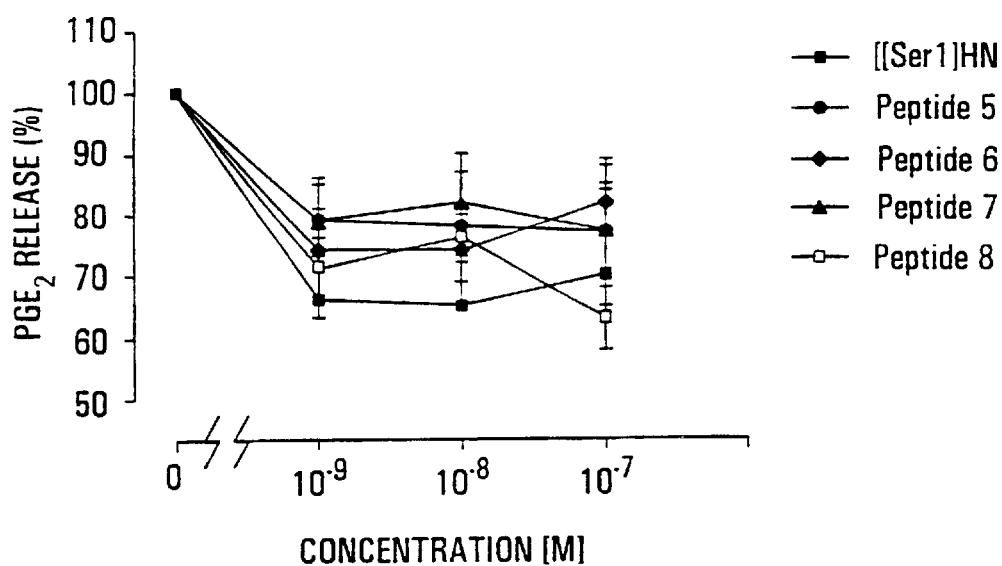
FIG. 7 shows the inhibitory effects of [Ser$^1$]HN, Peptide 5, Peptide 6, Peptide 7, and Peptide 8 on the LPS-induced production of prostaglandin E$_2$ by primary cultures of rat alveolar macrophages.

Relative potencies of tested peptides (i.c.v.) in producing analgesia in the mouse writhing pain assay calculated as percent of mice showing analgesia (method #1 in the examples section)

| Peptide | $ED_{50}$ (nmol/mouse) (95% CL)[a] | Potency ratio[b] (95% CL) |
|---|---|---|
| HN | 22.3 (12.1–41.1) | 1.0 |
| [Ser[1]]HN | 17.4 (7.0–43.0) | 1.3 (0.4–3.8) |
| H4-(86–100) | 4.1 (0.9–17.9) | 5.4 (0.7–40.1) |
| H4-(89–102)(OGP)[c] | 40.9 (25.8–65) | 0.5 (0.25–1.17) |
| 2 | 11.3 (4.2–30.4) | 2.0 (0.6–6.3) |
| 3 | 3.9 (1.7–9.1) | 5.7 (2.0–15.9) |
| 4 | 4.9 (1.8–13.2) | 4.5 (1.4–14.3) |
| 5 | 2.9 (0.8 –9.8) | 7.7 (1.3–46.6) |
| 13 | 7.5 (2.3 –24.4) | 3.0 (0.8–11.2) |

[a]95% Confidence limit.
[b]As compared with HN.
[c]OGP: osteoblastic growth peptide.
*$P \leq 0.05$ as compared with HN.

TABLE 2

Relative potency of tested peptides (i.c.v.) in producing analgesia in the mouse writhing pain assay as calculated as percent analgesia.

| Peptide | $AD_{50}$ (nmol/mouse) (95% CL)[a] | Potency ratio[b] (95% CL) |
|---|---|---|
| HN | 23.6 (12.4–45.0) | 1.0 |
| [Ser[1]]HN | 31.2 (18.5–52.6) | 0.75 (0.23–2.43) |
| H4-(86–100) | 22.7 (13.3–38.7) | 1.04 (0.32–3.38) |
| H4-(89–102)(OGP)c | 49.1 (33.0–73.1) | 0.48 (0.17–0.91) |
| 1 | 12.8 (3.6–46.1) | 1.84 (0.3–12.5) |
| 2 | 25.9 (5.9–113) | 0.91 (0.11–7.63) |
| 3 | 3.41 (0.8–14.6) | 6.92 (0.84–56.2)* |
| 4 | 12.7 (3.5–46.1) | 1.86 (0.27–12.8) |
| 5 | 13.3 (1.6–114) | 1.77 (0.11–28.1) |
| 5B | 25.3 (11.6–55.1) | 0.93 (0.22–3.9) |
| 6 | 25.1 (11.3–55.6) | 0.94 (0.22–3.98) |
| 7 | 4.21 (1.80–9.87) | 5.6 (1.25–25)* |
| 8 | 4.41 (1.7–11.9) | 5.35 (1.04–26.4)* |
| 9 | 2.23 (1.45–3.43) | 10.6 (3.6–31.0)* |
| 13 | 9.7 (2.5–37.4) | 2.43 (0.2–18) |

[a]95% Confidence limit.
[b]As compared with HN.
[c]OGP: osteoblastic growth peptide.
*$P \leq 0.05$ as compared with HN.

The following references are herein incorporated by reference.

1. Lemaire, S., Shukla, V. K., Rogers, C., Ibrahim, I. H., Lapierre, C. and Dumont, M. (1993). Isolation and characterization of histogranin, a natural peptide with N-methyl-D-aspartate antagonist activity. Or. J. Pharmacol. Molec. Pharm. Section. 245, 247–256.
2. Shukla, V. K., Lemaire, S., Dumont, M. and Merali, Z. (1995). N-methyl-D-aspartate receptor antagonist activity and phencyclidine-like behavioral effects of the pentadecapeptide, [Ser[1]] histogranin. Pharmacol. Biochem. Behav. 50, 49–54.
3. Rogers, C., and Lemaire, S. (1993). Characterization of [$^{125}$I] [Ser[1]] histogranin binding sites in rat brain. J. Pharmacol. Exp. Ther. 267, 350–356.
4. Dumont, M., Prasad, J. and Lemaire, S. (1994). Interaction of histogranin and related peptides with [$^3$H] dextromethorphan binding sites in rat brain. Neurosci. Lett. 173, 135–138.
5. Prasad, J. A., and Lemaire, S. (1997). Modulation by histogranin and related peptides of Gly potentiation of [$^3$H] MK-801 binding to rat brain membranes. Submitted.
6. Yamamoto, T., and Yaksh, T. L. (1992). Spinal pharmacology of thermal hyperalgesia induced by constriction injury of sciatic nerve. Excitatory amino acid antagonists. Pain 49, 121–128.
7. Ren, K., Williams, G. M., Hylden, J. L., Ruda, M. A., and Dubner, R., (1992). The intrathecal administration of excitatory amino acid receptor antagonists selectively attenuated carrageenan-induced behavioral hyperalgesia in rats. Or. J. Pharmacol. 219, 235–243.
8. Coderre, T. J. and Melzack, R. (1991). Central neural mediators of secondary hyperalgesia following heat injury In rats: neuropeptides and excitatory amino acids. Neurosci. Lett. 131, 71–74.
9. Coderre, T. J. and Van Empel, I. (1994). The utility of excitatory amino acid (EAA) antagonists as analgesic agents: comparison of the antinociceptive activity of various classes of EAA antagonists in mechanical, thermal, and chemical nociceptive tests. Pain 59, 345–359.
10. Wilcox, G. L., (1993), Spinal mediators of nociceptive neurotransmission and hyperalgesia:relationships among synaptic plasticity, analgesic tolerance and blood flow. APS J. 2, 265–275.
11. Trujillo, K. A. and Akil, H., (1991), Inhibition of morphine tolerance and dependence by the NMDA receptor antagonist MK-801. Science 251, 85–87.
12. Marek, P., Ben-Eliyahu, S. Vaccarino, A. L., Liebeskind, J. C., (1991), Delayed application of MK-801 attenuates the development of morphine tolerance in rats. Brain Res. 558, 163–165.
13. Elliot, K., Minami, N., Koleskinov Y. et al., (1994), The NMDA receptor antagonist, LY274614 and MK-801, and the nitric oxide synthetase inhibitor, $N^G$-nitro-L-arginine, attenuate analgesic tolerance to the mu opioid morphine but not to kappa opioids. Pain 56, 69–75.
14. Sagen, J., Wang, H. and Pappas, G. G., (1990), Adrenal medullary implants in the rat spinal cord reduce nociception in a chronic model of pain model. Pain 42, 69–79.
15. Wang, H. and Sagen, J., (1995), Attenuation of pain-related hyperventilation in adjuvant arthritic rats with adrenal medullary transplants in the spinal subarachnoid space. Pain 63, 313–320.
16. Sortwell, C. E., Pappas, G. D., and Sagen, J., (1995), Chromaffin cell xenografts in the rat neocortex can produce antidepressive activity in the forced swimming test. Exp. Brain Res. 103, 59–69.
17. Wang, H. and Sagen, J., (1994), Absence of appreciable tolerance and morphine cross-tolerance in rats with adrenal medullary transplants in the spinal cord. Neuropharmacology 33, 681–692.
18. Hama, A. T., Pappas, G. D., Sagen, J., (1996), Adrenal medullary implants reduce degeneration in the spinal cord of rats following chronic constriction of nerve injury. Exp. Neurology 137, 81–93.
19. Hama, A. T. and Sagen, J., (1994), Alleviation of neuropathic pain symptoms by xenogenic chromaffin cell grafts in the spinal subarachnoid space. Brain Res. 651, 183–193.
20. Siegan, J. B., Hama, A. T., and Sagen, J., (1996), Histogranin attenuates chronic pain induced by peripheral neuropathy, formalin-induced nociception and direct application of NMDA. Soc. Neurosci. 22, 1349.
21. Siegan J. B. and Sagen, J., (1997), A natural peptide with NMDA inhibitory activity reduces tonic pain in the formalin model. Neuroreport 8, 1379–1381.
22. Siegan, J. B., Hama, A. T. and Sagen, J., (1997), Suppression of neuropathic pain by naturally-derived peptide with NMDA antagonist activity. Brain Res. 755, 331–334.
23. Ruan, H., Prasad, J. and Lemaire, S., (1997), Central and peripheral non-opioid analgesic activity of histogranin and related peptides. Unsubmitted manuscript.
24. Mogil, J. C., Sternberg, W. F., Balian, H., Liebeskind, J. C. and Sudowski, B., (1996), Opioid and non-opioid swim stress-induced analgesia. A parametric analysis in mice. Physiol. Behav. 59, 123–133.
25. Lemaire, S., Griffiths, J., Lapierre, C., Lemaire, I., Merali, Z. and Ravindran, A. V., (1993), Characterization of histogranin receptors in human peripheral blood lymphocytes. Biochem. Biophys. Res. Commun. 194, 1323–1329.
26. Litchfield, J. T. and F. Wilcoxon, (1949), A simplified method of evaluating dose-effect experiments. J. Pharmacol. Exp. Ther. 96, 99.
27. Bab I., D. Gazit, M. Chorev, A. Muhlrad, A. Shteyer, Z. Greenberg, M. Namdar and M. Kahn, (1992), Histone H4-related osteogenic growth peptide (OGP): a novel circulating stimulator of osteoblastic activity. EMBO J. 11, 1867.
28. Hooke, L. P., L. He, and N. M. Lee, (1995), [Des-Tyr$^1$]dynorphin A-(2–17) has naloxone-insensitive antinociceptive effect in the writhing assay. J. Pharmacol. Exp. Ther. 273, 802.
29. E. Kaiser, Colescott, R. L., Bossingre, C. D. and Cook, P. I., (1970), Anal. Biochem., 595. U.S. Pat. No. 5,169,833.

What is claimed is:

1. A compound of Formula I:

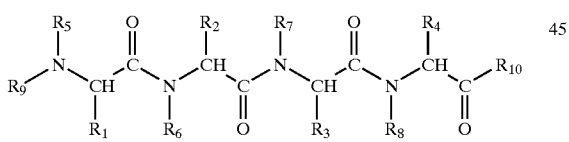

Formula I wherein $R_1$ represents hydrogen, alkyl, alkenyl, alkynyl, —$(CH_2)_n$—$NH_2$, —$(CH_2)_n$—NH—C(=NH)$NH_2$, or

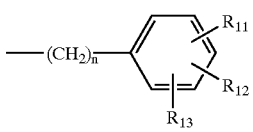

wherein "n" is an integer from 0 to 10;

$R_2$ represents —$(CH_2)_n CONH_2$, wherein "n" represents an integer from 0 to 10;

$R_3$ represents hydrogen, alkyl, alkenyl, alkynyl, the radical of formula:

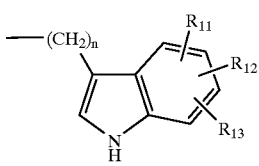

or the radical of formula:

wherein "n" represents an integer from 0 to 10; and
$R_{11}$, $R_{12}$ and $R_{13}$ may be the same or different and represent hydrogen, alkyl, alkenyl, alkynyl, —I, —F, —Br, —Cl, or —OH; and $R_4$ represents —$(CH_2)_n NH_2$, —$(CH_2)_n NHC(=NH)NH_2$, or

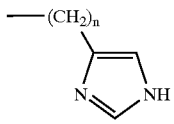

wherein "n" represents an integer from 0 to 10;

$R_5$ and $R_9$ may be the same or different and represent hydrogen, alkyl, alkenyl, alkynyl, alkylcarbonyl, aminocarbonyl, alkylaminocarbonyl, dialkylaminocarbonyl, dialkylamino, or —$(CH_2)_n$aryl, wherein "n" is an integer from 1 to 10;

$R_6$, $R_7$, and $R_8$ may be the same or different and represent hydrogen, alkyl, alkenyl, or alkynyl;

$R_{10}$ represents hydroxy, alkoxy, alkenyloxy, alkynyloxy, amino, alkylamino, dialkylamino, alkylaryl, arylalkoxy, aryloxy, alkoxyaryl, $A_1$, $A_1$-$A_2$, $A_1$-$A_2$-$A_3$, $A_1$-$A_2$-$A_3$-$A_4$, or, $A_1$-$A_2$-$A_3$-$A_4$-$A_5$, wherein $A_1$ represents threonine or serine;

$A_2$ represents leucine, glycine, alanine, valine, or isoleucine;

$A_3$ represents tyrosine, phenylalanine, or tryptophan;

$A_4$ represents glycine, alanine, leucine, isoleucine, or valine; and $A_5$ represents phenylalanine, tyrosine, or tryptophan; or pseudopeptide analogues thereof wherein one or more of the carbonyl groups of the peptide linkage is replaced by —C(=S)— or by —$CH_2$—, and/or wherein one or more of the amide bonds, —C(O)—NH—, is replaced by the retro-inverso form, —NH—C(O)—, thereof; and pharmaceutically acceptable salts and esters thereof, with the proviso that the compound is not selected from the group consisting of:

H-glycine-glutamine-glycine-arginine-threonine-leucine-tyrosine-glycine-phenylalanine (SEQ ID NO: 16);

H-valine-glutamine-tryptophan-lysine (SEQ ID NO: 18);

H-histidine-asparagine-leucine-lysine (SEQ ID NO: 19);

H-leucine-glutamine-Ψ(CS—NH)leucine-lysine (SEQ ID NO: 20);

H-lysine-glutamine-phenylalanine-lysine (SEQ ID NO: 21); and

H-glycine-glutamine-leucine-lysine (SEQ ID NO: 22).

2. A compound of Formula II:

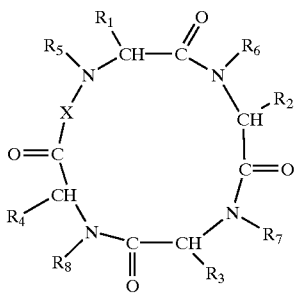

Formula II wherein $R_1$, $R_2$, $R_3$, $R_4$, $R_5$, $R_6$, $R_7$, and $R_8$, are as defined in claim 1; and X represents an amino acid or peptide fragment represented by $A_1$, $A_1$-$A_2$, $A_1$-$A_2$-$A_3$, $A_1$-$A_2$-$A_3$-$A_4$, or $A_1$-$A_2$-$A_3$-$A_4$-$A_5$, wherein $A_1$, $A_2$, $A_3$, $A_4$, and $A_5$ are as defined in claim 1; or a divalent group of formula:

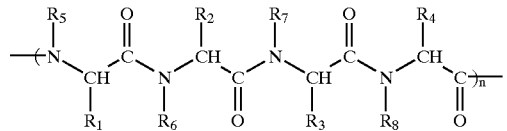

wherein "n" represents an integer from 0 to 10; and $R_1$, $R_2$, $R_3$, $R_4$, $R_5$, $R_6$, $R_7$, and $R_8$ are as defined in claim 1;

pseudopeptide analogues thereof wherein one or more of the carbonyl groups of the peptide linkage is replaced by —C(=S)— or by —$CH_2$—, and/or wherein one or more of the amide bonds, —C(O)—NH—, is replaced by the retro-inverso form, —NH—C(O)—, thereof; and pharmaceutically acceptable salts and esters thereof.

3. A compound according to claim 1, of Formula III:

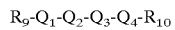

wherein $Q_1$ represents glycine, alanine, valine, leucine, isoleucine, lysine, histidine, or arginine;

$Q_2$ represents asparagine or glutamine;

$Q_3$ represents glycine, alanine, valine, leucine, isoleucine, phenylalanine, tryptophan, or tyrosine;

$Q_4$ represents lysine, arginine, or histidine;

$R_9$ represents hydrogen; and $R_{10}$ represents hydroxy;

pseudopeptide analogues thereof wherein one or more of the carbonyl groups of the peptide linkage is replaced by —C(=S)— or by —$CH_2$—, and/or wherein one or more of the amide bonds, —C(O)—NH—, is replaced by the retro-inverso form, —NH—C(O)—, thereof; and pharmaceutically acceptable salts and esters thereof.

4. A compound according to claim 2, of Formula IV:

Formula IV

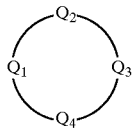

wherein $Q_1$ represents glycine, alanine, valine, leucine, isoleucine, lysine, histidine, or arginine;

$Q_2$ represents asparagine or glutamine;

$Q_3$ represents glycine, alanine, valine, leucine, isoleucine, phenylalanine, tryptophan, or tyrosine; and $Q_4$ represents lysine, arginine, or histidine;

pseudopeptide analogues thereof wherein one or more of the carbonyl groups of the peptide linkage is replaced by —C(=S)— or by —$CH_2$—, and/or wherein one or more of the amide bonds, —C(O)—NH—, is replaced by the retro-inverso form, —NH—C(O)—, thereof; and pharmaceutically acceptable salts and esters thereof.

5. A compound according to claim 3, wherein $Q_1$ represents glycine or arginine;

$Q_2$ represents L-glutamine or D-glutamine;

$Q_3$ represents glycine, alanine, or tyrosine;

$Q_4$ represents L-arginine or D-arginine;

$R_9$ represents hydrogen; and $R_{10}$ represents hydroxy;

pseudopeptide analogues thereof wherein one or more of the carbonyl groups of the peptide linkage is replaced by —C(=S)— or by —CH$_2$— and/or wherein one or more of the amide bonds, —C(O)—NH—, is replaced by the retro-inverso form, —NH—C(O)—, thereof; and pharmaceutically acceptable salts and esters thereof.

6. A compound according to claim 2, wherein $Q_1$ represents glycine or arginine;

$Q_2$ represents L-glutamine or D-glutamine;

$Q_3$ represents glycine, alanine, or tyrosine;

$Q_4$ represents L-arginine or D-arginine;

pseudopeptide analogues thereof wherein one or more of the carbonyl groups of the peptide linkage is replaced by —C(=S)— or by —CH$_2$—, and/or wherein one or more of the amide bonds, —C(O)—NH—, is replaced by the retro-inverso form, —NH—C(O)—, thereof; and pharmaceutically acceptable salts and esters thereof.

7. A compound selected from the group consisting of cyclic(-Gly-Gln-Tyr-Arg-) (SEQ ID NO: 7), cyclic(-Gly-Gln-Tyr-D-Arg-), cyclic(-Gly-D-Gln-Tyr-D-Arg-), H-Gly-Gln-Tyr-Arg-OH (SEQ ID NO: 8), H-Gly-Gln-Tyr-D-Arg-OH, and H-Gly-D-Gln-Tyr-D-Arg-OH.

8. Cyclic(-Gly-Gln-Tyr-D-Arg-).

9. Cyclic(-Gly-D-Gln-Tyr-D-Arg-).

10. A pharmaceutical composition for the treatment of pain, comprising a compound according to claim 1 or 2, in admixture with a suitable pharmaceutically acceptable diluent or carrier.

11. A method for treating pain, comprising administering to a subject in need thereof a therapeutically effective amount of a compound according to claim 1 or 2.

12. A commercial package which contains the compound according to claim 1 or 2, together with instructions for the use thereof for treatment of pain.

* * * * *

UNITED STATES PATENT AND TRADEMARK OFFICE
CERTIFICATE OF CORRECTION

PATENT NO. : 6,566,327 B1
DATED : May 20, 2003
INVENTOR(S) : Simon Lemaire

It is certified that error appears in the above-identified patent and that said Letters Patent is hereby corrected as shown below:

Column 4,
Line 64, after, "–NH–C(O)–", insert -- thereof; and --.

Column 10,
Line 50, replace "com pound" with -- compound --.

Column 13,
Cancel lines 47 to 49.

Column 18,
Line 18, cancel "U.S. Pat. No. 5,169,833" and insert, starting on a new line, -- 30. U.S. Pat. No. 5,169,833. --

Signed and Sealed this

Ninth Day of March, 2004

JON W. DUDAS
*Acting Director of the United States Patent and Trademark Office*